United States Patent [19]

Forsström et al.

[11] Patent Number: 4,492,139
[45] Date of Patent: Jan. 8, 1985

[54] DEVICE IN A MICROTOME FOR RELATIVE MOVEMENT BETWEEN THE KNIFE AND SPECIMEN HOLDER

[75] Inventors: Bo Forsström, Järfälla; Tomas Luniewski, Stockholm; Per Wikefelt, Järfälla, all of Sweden

[73] Assignee: LKB-Produkter, Bromma, Sweden

[21] Appl. No.: 314,969

[22] Filed: Oct. 26, 1981

[30] Foreign Application Priority Data

Oct. 27, 1980 [SE] Sweden ............................ 8007527

[51] Int. Cl.³ ............................................. G01N 1/06
[52] U.S. Cl. .................................. 83/727; 83/414; 83/589; 83/915.5
[58] Field of Search ............... 83/915.5, 414, 714, 83/716, 730, 727, 589

[56] References Cited

U.S. PATENT DOCUMENTS 3,453,919 7/1969 Ehrat et al. ..................... 83/589
3,771,405 11/1973 Blum ............................. 83/915.5

FOREIGN PATENT DOCUMENTS 192431 11/1967 U.S.S.R. ....................... 83/915.5
584223 6/1975 U.S.S.R. ....................... 83/915.5

OTHER PUBLICATIONS

"Handbok I Finmekanik", by Bartil Ejerhed (translated version with illustrations reproduced by photocopy), FIGS. 453, 454 on p. 6 especially.

Primary Examiner—Frank T. Yost
Assistant Examiner—Hien H. Phan
Attorney, Agent, or Firm—Fisher, Christen & Sabol

[57] ABSTRACT

Device in a microtome in which a knife (1) and a specimen (2) are displaceable with respect to one another in two perpendicular planes, one of which is parallel to the cutting surface and the other is parallel to the knife edge, for obtaining a cutting movement or a feeding movement in the microtome, the device being used for obtaining at least one of these movements, the device consisting of at least one spring link (30) in which the moveable part (5) is suspended whereby the link consists of at least two in said plane located crossed leaf springs (27, 28, 29) and driving means (7, 8) arranged between the moveable part and the casing of the microtome (3) so as to achieve said displacement.

10 Claims, 4 Drawing Figures

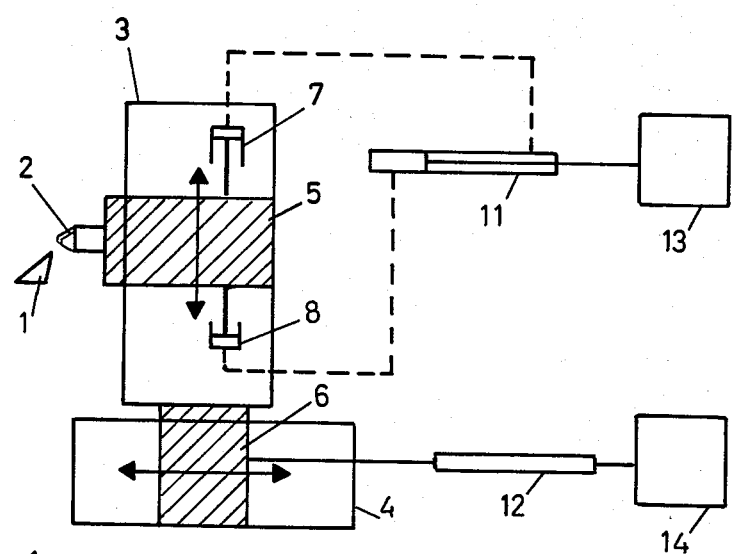
Fig. 1
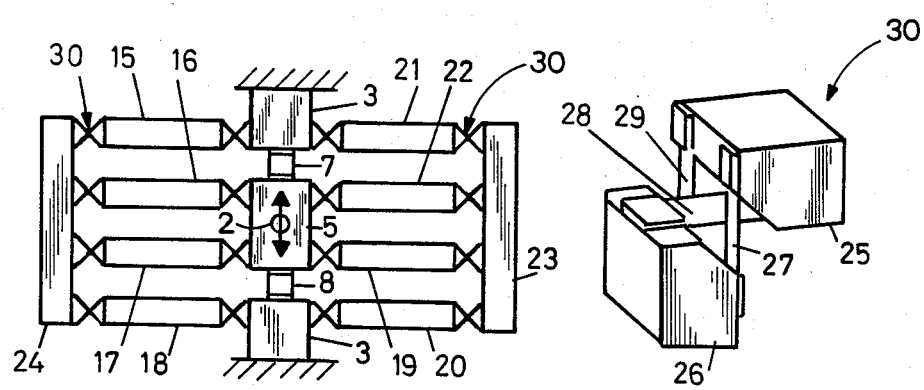
Fig. 3
Fig. 4

DEVICE IN A MICROTOME FOR RELATIVE MOVEMENT BETWEEN THE KNIFE AND SPECIMEN HOLDER

BACKGROUND OF THE INVENTION

The present invention refers to a device in a microtome in which a knife and a specimen are displaceable with respect to each other in two perpendicular planes so as to achieve a cutting movement and a feeding movement in the microtome.

In microtomes and ultramicrotomes, respectively, which are instruments for producing sample cuts to be studied in a microscope or an electron microscope, respectively, the sample cuts are produced by moving the sample block towards a knife edge from which the sample cut is cut off. This movement is repeated several times, the sample block being displaced between each cut, the size of this displacement being dependent upon the desired thickness of the cut.

In order to obtain the cutting movement the sample block is usually attached to one end of a long heavy arm, the opposite end of which can be tilted around an axis parallel to the knife edge. The long arm thereby makes the instrument long and space consuming. Furthermore, the cutting is carried out by means of letting the arm fall down subject to the gravity forces which means that the arm must be relatively heavy in order to obtain sufficient cutting forces.

SUMMARY OF THE INVENTION

It is an object of the present invention to achieve a device in a microtome in which the above mentioned drawbacks are eliminated. Thus, the device according to the invention makes it possible to design a microtome having a low weight and a small volume and in which the cutting forces can be made arbitrarily large.

BRIEF DESCRIPTION OF THE DRAWINGS

The invention will now be explained in detail, reference being made to the enclosed drawings in which:

FIG. 1 is a schematic side view of a microtome using the device according to the invention;

FIG. 3 is a schematic side view of a modification of the device according to the invention; and FIG. 4 is a perspective fragmentary enlarged view of a crossed spring link to be used in the device according to the invention.

DETAILED DESCRIPTION OF THE INVENTION

Figure 2:
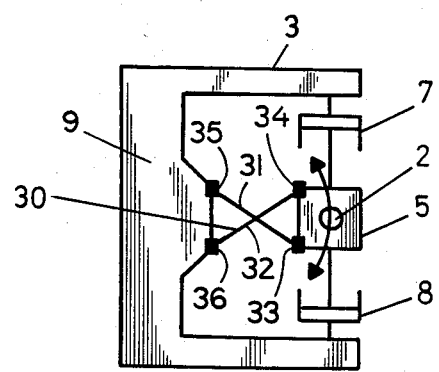
FIG. 2 is a schematic side view of a device according to the invention for achieving a cutting movement of a specimen block.

In FIG. 1 which schematically shows a microtome using the device according to the invention, a knife 1 is disposed adjacent the edge of a specimen block 2, which is displaced by means of a device 3 according to the invention. The device 3 is provided with a vertically moveable specimen block holder 5 which is operated by two hydraulic or pneumatic driving units 7, 8 which in turn are operated by a driving unit 11 connected to the units 7, 8 by flexible hoses (unnumbered). The unit 11 contains a plunger positionable by a reversible step motor 13. For feeding the specimen 2 the device 3 is located on and attached to a horizontally moveable part 6 of a fixed feeding unit 4. The part 6 is displaceable by means of a feeding screw 12 which is positioned by a reversible step motor 14.

In a preferred embodiment of the invention the unit 3 is as shown in FIG. 2, and the same reference numerals are used as in FIG. 1. The moveable specimen block holder 5 is hingedly linked to frame 9 of unit 3 by a crossed leaf spring link arrangement 30, known per se, acting as a hinge and comprising at least two crossed leaf springs 31,32. Ends 33 and 34, respectively, of the springs 31,32 are connected to movable specimen block holder 5 and the other ends 35,36, respectively, are connected to frame 9. The planes of the leaf springs 31,32 are perpendicular to the plane of FIG. 2, giving a horizontal hinge access around which holder 5 can swing in a vertical plane, as shown by the arrows in FIG. 2. The device shown in FIG. 2 thus keeps the specimen vertically disposed during the complete cutting movement and furthermore, the hydraulic or pneumatic driving means is used to apply any desired forces to the movable specimen block holder 5 without using a suspension having a large mass.

In FIG. 4, a perspective view of the cross spring link 30 which is conventional and known per se, is shown. The general design of cross spring link 30 is suitable for use in connection with the present invention. As shown, the cross leaf spring link arrangement 30 comprises 3 leaf springs 27,28,29 interconnecting two elements 25,26. With reference to FIG. 2, element 25 corresponds to holder 5, and element 26 corresponds to frame 9 of unit 3.

The device shown in FIG. 2 allows a curvilinear arc of travel block 5. To avoid such travel, an alternative embodiment is shown in FIG. 3. There, a plurality of crossed spring links 30 makes it possible to obtain a flat, vertical uncurved movement of the sample holder block 5. As shown in FIG. 3 the specimen holder block 5 is supported by four crossed spring links connected to four rigid arms 16, 17, 19, 22 which in turn are supported by crossed spring links connected to two vertical side pieces 23,24. The side pieces 23,24 are in a corresponding way connected to the casing 3 by crossed spring links and additional rigid arms 15, 18, 20, 21. This type of device is also suitable to be used for the feeding movement, i.e. the device denoted 4 in FIG. 1.

In FIG. 4, as discussed above, is shown an enlarged fragmentary view of a crossed spring link 30 known per se and suitable for use in the device according to the invention. As shown in the figure the two arms 25 and 26 are connected by three springs 27, 28, 29.

The improved device in a microtome of the present invention is capable of achieving the above-enumerated objects and while preferred embodiments of the present invention have been disclosed, it will be understood that it is not limited thereto but may be otherwise embodied within the scope of the following claims.

We claim:

1. In a microtome of the type wherein a knife and a specimen holder comprise two relatively movable members for cutting extremely thin successive sections from a specimen the improvement which comprises mounting means for said two members for reciprocatory relative movement between the two members in a first plane and for relative incremental feeding movement between the two members in a plane disposed transversely with respect to said first plane;

said reciprocatory and feeding movements being disposed in respective straight lines normal to the line of intersection of said transversely disposed planes;

one of said two relatively movable members is hingedly connected to one end of each of a first two pairs of rigid parallel arms disposed in the plane of movement of said one member, the respective pairs of said arms extending outwardly from said one member in opposite directions from each other for hinged connection at their respective other ends to two remotely disposed elongated intermediate support elements extending generally parallel with the direction of said movement, said support elements being, in turn, hingedly connected to one end of each of a second two pairs of rigid parallel arms disposed in the plane of movement of said one member, the respective other ends of the second two pairs of arms being inwardly disposed for hinged connection to respectives ones of a pair of support portions of a unit adapted to support said one member for said reciprocating relative movement.

2. Device according to claim 1, wherein hinged connections comprised at least three leaf springs, the respective ends of each spring being fixed to a respective one of the connected elements, at least two of the leaf springs being disposed in a common plane, and a third leaf spring being disposed in a plane angularly related to the plane of said two springs.

3. Device according to any one of claims 1, or 2, wherein fluid power means is connected between at least one of said relatively movable members and a casing of the microtome for imparting said relative movement.

4. Device according to claim 3, wherein said fluid comprises a gas.

5. Device according to claim 4, wherein said fluid power means includes a plunger means connected to said relatively movable member, gas pump means to supply said plunger means and electric step motor means for operating the pump means.

6. Device according to claim 3, wherein said fluid comprises a liquid.

7. Device according to claim 6, wherein said fluid power means includes a plunger means connected to said relatively movable member, hydraulic pump means to supply said plunger means and electric step motor means for operating the pump means.

8. A microtome comprising a casing, a stationary knife and a movable specimen holder mounted therein and driving means for moving said specimen holder relative to the knife for cutting extremely thin successive sections from a specimen on said holder, wherein the specimen holder is suspended in a frame (9) by means of at least one crossed leaf spring link so as to be movable in a vertical plane for providing vertical cutting movement to obtain a cut in a plane parallel to said vertical plane, said frame being mounted in the casing on a horizontally movable part of feeding means for providing horizontal incremental feeding movement of said specimen holder perpendicularly to said vertical plane, and said driving means comprise power means operating between the specimen holder and said frame.

9. A microtome as claimed in claim 8, wherein said power means comprises fluid power means.

10. A microtome as claimed in claim 8 or 9, wherein the specimen holder is suspended in said frame by being hingedly connected to one end of each of a first two pairs of rigid parallel arms disposed in the vertical plane, the respective pairs of said arms extending outwardly from said member in opposite directions from each other for hinged connection at their respective other ends to two remotely disposed elongated intermediate support elements extending generally parallel with the direction of said vertical cutting movement, said support elements being, in turn, hingedly connected to one end of each of a second two pairs of rigid parallel arms disposed in the plane of movement of said one member, the respetive other ends of the second two pairs of arms inwardly disposed for hinged connection to said frame, the hinged connections being crossed leaf spring links.

* * * * *